United States Patent [19]

Longman, Jr.

[11] 4,078,211

[45] Mar. 7, 1978

[54] METHOD AND APPARATUS FOR BALANCING PARTICLE DETECTING SIGNALS GENERATED IN A PARTICLE STUDY DEVICE HAVING MULTIPLE APERTURES

[75] Inventor: Millard D. Longman, Jr., Hialeah, Fla.

[73] Assignee: Coulter Electronics, Inc., Hialeah, Fla.

[21] Appl. No.: 727,959

[22] Filed: Sep. 29, 1976

[51] Int. Cl.² ............................................. G01N 27/00
[52] U.S. Cl. .............................. 324/71 CP; 235/92 PC; 128/2 G
[58] Field of Search .............. 324/71 CP; 235/92 PC; 356/39, 72, 73; 23/230 R, 230 A; 128/2 G

[56] References Cited

U.S. PATENT DOCUMENTS

| | | | |
|---|---|---|---|
| 3,549,994 | 12/1970 | Rothermel et al. | 324/71 CP |
| 3,567,321 | 3/1971 | Hogg | 356/72 |
| 3,836,850 | 9/1974 | Coulter | 324/71 CP |
| 3,882,385 | 5/1975 | Coulter et al. | 324/71 CP |
| 3,949,197 | 4/1976 | Bader | 235/92 PC |

Primary Examiner—Rudolph V. Rolinec
Assistant Examiner—Vincent J. Sunderdick
Attorney, Agent, or Firm—Silverman & Cass

[57] ABSTRACT

In multiple aperture electronic particle detecting apparatus, there are variations in the physical construction of the apertures intended to be identical, as a result of which the signals produced by the identical sized particle, if passed through all of the apertures, will not be identical. Each apparatus in which a multiple aperture arrangement is used requires many adjustments to be made in balancing the apparatus to compensate for the variations in the signals produced. A method and electronic circuit are disclosed which enable simplified balancing of the detecting means of the apparatus without the need for the many adjustments required heretofore. Particles of unknown size in suspension are passed through the apertures and the current supplied to all but one of the apertures is adjusted to render the signals produced of equal amplitude. The detecting means may be balanced by passing particles of a known suspension, which have a known size, through the apertures and adjusting the current supplied to all but one of the apertures to render the signals produced of equal amplitude. It is immaterial whether the particles are monosized or have a moderately broad size distribution.

10 Claims, 1 Drawing Figure

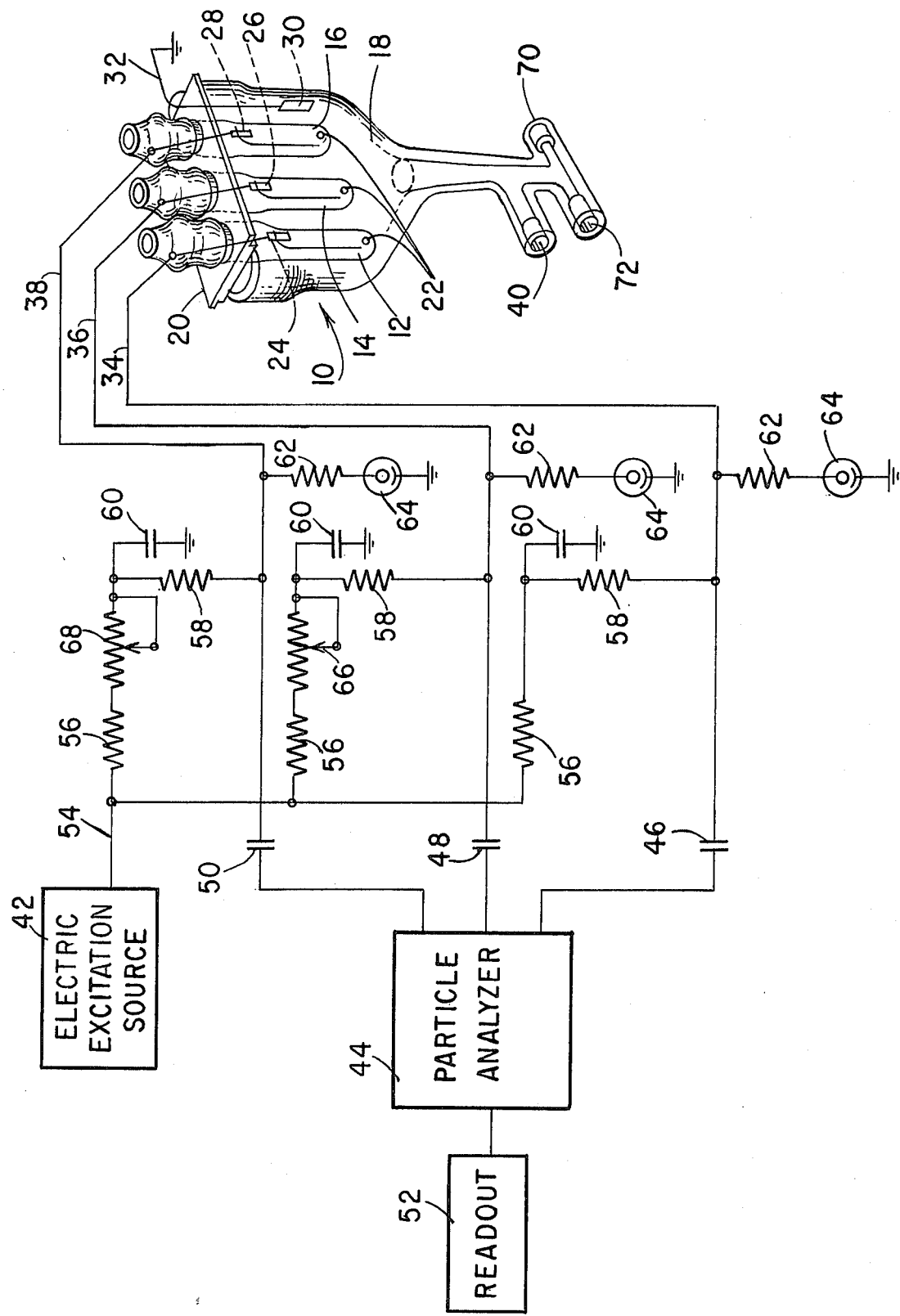

METHOD AND APPARATUS FOR BALANCING PARTICLE DETECTING SIGNALS GENERATED IN A PARTICLE STUDY DEVICE HAVING MULTIPLE APERTURES

CROSS REFERENCE TO RELATED PATENTS

Patents incorporated by reference are U.S. Pat. Nos. 3,444,463 and 3,549,994. Reference is also made to U.S. Pat. Nos. 3,259,842 and 3,502,974. All of these patents are assigned to the assignee of the instant application.

BACKGROUND OF THE INVENTION

This invention relates generally to particle study devices having multiple apertures through which particles suspended in a fluid are passed and more particularly is concerned with balancing the individual signals produced by equal sized particles passing through each of the apertures to eliminate the variations in the signals caused by the physical differences between apertures.

A particular device for studying particles of microscopic size suspended in a fluid of electrolyte whose electrical impedance or resistivity is substantially different from that of the particles is shown and described in U.S. Pat. No. 3,259,842. The fluid is passed through a microscopic aperture formed in an insulating wall. Simultaneously, an electrical current is established in the aperture providing a sensing zone whose impedance is changed in proportion to the size of the particle passed through the zone. The change in impedance is detected and a signal is generated whose amplitude is proportional to the particle size and whose duration is equal to the time that it required for the particle to pass through the sensing zone.

The signals can be counted for any given volume of suspension passed through the zone to determine the particle concentration or the signals can be segregated according to size and number to determine the particle size distribution of the suspension. The particle information derived from the signals is utilized in hospitals and laboratories and it is extremely critical that the information be accurate. The devices are typically utilized in large complex apparatus whose operators do not have the time and/or may not have the expertise constantly to monitor and correct every phase of operation of the apparatus.

Various types of apparatus have been developed to overcome such problems as an aperture being blocked by particles or other problems which cause erroneous information to be developed. One device developed to overcome the problems presented in employing a single aperture device is shown in U.S. Pat. No. 3,444,463 which is incorporated herein by reference.

In this system the sample fluid is passed through three apertures simultaneously and separate respective detecting signals are developed in response to the particles passing through each of the three apertures. The signals developed by each aperture are compared and then by a process commonly known as "voting", should one of the signals developed be beyond a predetermined limit from the average of the other two signals, that aperture is considered to be malfunctioning and the signal from that aperture is ignored in the processing of information using such signals.

The probability of more than one aperture becoming blocked or otherwise malfunctioning at the same time is remote. The reliability of the information received from the particle study is thus enhanced as a blocked or otherwise faulty aperture is ignored in the study.

A system utilizing the multiple apertures and voting as described above is disclosed in U.S. Pat. No. 3,549,994 which is also incorporated herein by reference. This system was developed especially for use in the field of medicine and biology for studying body fluids. As is well known body fluids such as blood are studied to obtain information to be used in the diagnosis and treatment of patients. The need for accuracy of this information is thus very critical.

Blood is composed of microscopic cells or particles suspended in a serum and various of these cells are important in the study of the blood. Three types of blood cells may be of particular interest including red and white blood cells which are on the order of seven or more microns in size and platelets which may range from one to four microns in size.

There are several important parameters involving these cells which are utilized in the diagnosis and study of the blood. Three of these parameters are the red blood cell count (RBC), the white blood cell count (WBC) and the mean corpuscular volume (MCV). These parameters are directly measured in the system described in U.S. Pat. No. 3,549,994.

The features of these systems are incorporated in a commercial system sold throughout the world as a COULTER COUNTER® particle analyzing instrument (the mark COULTER COUNTER® is the Registered Trademark, Registration Number 679,591 of Coulter Electronics, Inc. of Hialeah, Florida).

In the systems utilizing multiple apertures and voting, the need for accuracy of the detecting signals developed by the passage of the particles through each aperture is extremely important. If the signals which are "voted" on by the voting apparatus are not equal for the same sized particles for any reason when the circuitry may vote an aperture which is functioning normally. Even if the signal differences are not sufficient for one aperture to be voted out the resultant data and information developed in the particular study will not be accurate.

A determination of the RBC, WBC and MCV has required eight adjustments heretofore to avoid having a normally functioning aperture voted out and to develop accurate data. The three amplifiers, commonly called "pre-amps", for the white cell and the three amplifiers for the red cell study were individually adjusted at some low gain point by attenuation to balance the system.

Two of the output signals from the three red cell amplifiers are utilized to determine MCV. Two more attenuating adjustments were made, heretofore, to balance the MCV output. This made a total of eight adjustments, each of them attenuating the output signals and changing the signal to noise ratio of the electronic circuits.

The severity of the requirements of balancing the systems is greater when smaller cells such as the platelets of one to four micron size are required to be detected. The apertures in the above systems typically have had a diameter on the order of 100 to 150 microns. To obtain a better volume distribution and to increase the sensitivity of the devices to detect the smaller particles apertures of 50 microns in diameter have been used and are now being contemplated for universal use in these devices.

The apertures are formed in wafers of sapphire or ruby and have typical manufacturing tolerances of approximately one micron. This variation in the aperture size becomes critical because, using the circuitry in U.S. Pat. No. 3,259,842, the amplitude of the signal developed in response to a given size particle passing through an aperture is inversely related to the square of the diameter of the aperture. The peak signal amplitude is directly related to particle volume.

When apertures are utilized in parallel in multiple aperture systems the variance in signals caused by different aperture sizes must be corrected. As noted above the actual electronic gain of each following circuit (such as the amplifiers) might be adjusted; however, this also changes the output noise component of the signals generated. Ideally, the signal to noise ratio should be optimized and henceforth left unaltered. Utilizing 100 micron apertures with a one micron tolerance in diameter and length there exists on the order of a three percent error in the gain between the apertures when they are used in parallel.

In utilizing fifty micron apertures, however, the one micron manufacturing tolerance is equivalent to a possible six percent gain error between the three apertures used in parallel.

It would thus be desirable to balance the signals developed by equal sized particles passing through the parallel apertures without decreasing the sensitivity of the circuits which produce the necessary and critical information from the detected signals.

SUMMARY OF THE INVENTION

A particle study device has balancing means for adjusting the current passed through all but one of the apertures. An electric current is passed through each of the apertures which results in a signal to be generated upon passage of a particle in suspension through said aperture. Respective detecting signals are thus generated in response to the particles passing through all of the apertures. To balance the device known or unknown sized particles are passed through the apertures and the electric currents passing through all but one of the apertures are adjusted substantially to equalize the detecting signals generated from the particles passing through each aperture.

BRIEF DESCRIPTION OF THE DRAWING

The drawing is a partial block and partial schematic diagram of a particle study device embodying the system of this invention.

DESCRIPTION OF THE PREFERRED EMBODIMENT

As indicated above, the invention is concerned with a method and apparatus for balancing a particle detecting apparatus of the type which uses an arrangement wherein there is an assembly of a plurality of aperture tubes all suspended in a single vessel of suspension. The suspension is sucked from the vessel into all of the aperture tubes through their respective apertures and individual detecting circuits capable of producing independent signals when a particle passes through its respective aperture are respectively coupled to the tubes. Thus, all of the aperture tubes and their respective associated detecting circuits are producing signals while the apparatus is operating.

For the proper operation of the apparatus and to enable accurate data or information to be obtained therefrom it is essential that the amplitude of a signal produced from a given sized particle be proportional to the size of that particle and, in addition, that the actual amplitude of that same signal be identical for all aperture tubes and their respective associated circuits if that identical particle had passed through the apertures thereof.

The invention herein provides a method and apparatus for obviating the adjustments previously required and problems caused thereby in balancing the apparatus which have been alluded to above.

"Balancing", as used herein is intended to mean passing a suspension of particles through the apertures and adjusting the current passing through all but one of the apertures to equalize the individual signals generated by the particles passing through each one of the apertures. Thus "balancing" may be just adjusting the sensitivities of the signals produced by each channel to eliminate the differences caused by the physical differences of the apertures themselves.

Referring now to the drawing, the glass vessel mentioned above is shown generally at 10 containing a suspension of particles to be studied. Three aperture tubes 12, 14 and 16 are immersed in a main body 18 of the vessel 10, being mounted on a plate 20 which engages the upper entrance of the vessel 10 as a sort of closure.

Each of the aperture tubes 12, 14 and 16 has a microscopic aperture 22 in the bottom end and individual electrodes 24, 26 and 28 which enable the individual detecting circuits to be coupled to the body of suspension contained in the respective aperture tubes. The vessel 10 has an electrode 30 common to all of the electrodes in the aperture tubes and coupled by a lead 32 to ground. Leads 34, 36 and 38 extend from the respective electrodes 24, 26 and 28 to the individual electronic detecting circuits.

The suspension may be admitted into the vessel 10 by means of a sample conduit 40, and each of the aperture tubes is coupled to a suitable source of negative pressure (not shown) so that the suspension is being sucked into all the aperture tubes simultaneously by way of the respective apertures when the apparatus is in operation.

An electric excitation source 42 is coupled to each of the leads 34, 36, 38 and hence to the respective electrodes 24, 26 and 28. Electric current passes through the respective apertures to the common lead 32 and hence to ground. The current passing through the suspension in each aperture will produce a volume of relatively high current density compared to the current density elsewhere in the suspension thereby establishing the above-mentioned sensing zones in the respective apertures and their immediate vicinities.

Since the suspension is chosen to be of a substantially different impedance than the particles suspended therein, as the particles pass through each of the apertures they displace a finite amount of the suspension and hence vary the impedance by a finite amount in each sensing zone.

This change in impedance may be detected in the individual circuits in a particle analyzer 44 which is coupled to the respective apertures 34, 36 and 38 through coupling capacitors 46, 48 and 50. The coupling capacitors couple the signals due to the changes in impedance to the particle analyzer 44 but at the same time prevent the excitation current from the electric excitation source 42 from affecting the circuits in the particle analyzer.

The particle analyzer 44 may be of the type described in cross-referenced U.S. Pat. No. 3,549,994. The variations in impedance in each sensing zone will cause an independent detecting signal to be developed indicative of the particle passing through the respective aperture or sensing zone. The signals from the three sensing zones will then be compared by the voting circuitry as previously described. The resulting data or information derived from the signals from the properly operating apertures may be displayed on a readout device 52 or otherwise processed and used.

In the prior systems the electric excitation source 42 was adjusted for a proper amplitude current passing through the apertures 22. This adjustment did not enable any compensation for variances in the aperture diameters, because the electric excitation source is coupled over a common lead 54 to each of the electrodes 24, 26 and 28. Any adjustment of the electric excitation source 42 thus affected the current passing through each aperture and was not individually adjustable.

The prior art configuration coupling the electric excitation source 42 and the common lead 54 to the individual electrode leads 34, 36 and 38 comprises two fixed resistors 56 and 58 and a capacitor 60 in each lead. The capacitors 60 are utilized to eliminate any noise emanating from the electric excitation source 42 before it can interfere with the sensing zones.

Each of the leads 34, 36 and 38 is also provided with gaseous discharge device protection circuits. Each protection circuit comprises a resistor 62 and a gaseous discharge device such as a neon lamp 64 coupled between ground and each lead. These are standard protection circuits as known in the art and the values of the resistors and specifications of the neon lamps are chosen such that the neon lamp will discharge at a predetermined voltage and current. This current will be exceeded when an aperture is blocked, when the sample is removed below the aperture in the vessel 10, or when the aperture tubes themselves are withdrawn from the vessel 10. The discharge of the neon tubes prevents damage to the coupling capacitors 46, 48 and 50 and the circuits in the particle analyzer 44 by amplitudes greater than their respective operating ranges.

To eliminate the balancing problems previously discussed, a variable impedance or potentiometer was added in each of two aperture current paths. These potentiometers 66 and 68 were added to the current path between the electric excitation source 42 and leads 36 and 38. This arrangement enables the currents passing through respective leads 36 and 38 to be adjusted individually and independently of any adjustment of the electric excitation source 42.

The electric excitation source 42 preferably is a voltage source as shown in the FIGURE; however it may be other suitable types of excitation sources. For instance, the electric excitation source 42 may be a current source, in which case the potentiometers 66 and 68 would be placed in parallel with the apertures rather than in series as shown in the FIGURE. The electric excitation source also may be a varying frequency source, for example, as described in U.S. Pat. No. 3,502,974.

The balancing of the device will now be described. A suspension or sample fluid containing particles is introduced into the body of the vessel 10 through the sample conduit 40. The suspension is then sucked through the apertures 22 of all three aperture tubes while simultaneously electric current is passing through the apertures from the electric excitation source 42. As each particle from the main body of suspension passes through one of the apertures the impedance in the respective sensing zone will vary. This is detected by its individual detecting circuit in the particle analyzer 44 by means of the respective leads 34, 36 and 38. The amplitudes of the individual detecting signals caused by the particles passing through each of the sensing zones are then compared. The signal amplitudes generated should be substantially equal.

The detecting signal developed from lead 34 is used as the balancing standard for the other two signals. The detecting signal developed in response to the modulation on lead 34 caused by the particles passing through its sensing zone may be adjusted by changing the current supplied by electric excitation source 42. This, of course, also changes the signals developed from the other sensing zones on the leads 36 and 38.

Once the signal developed from lead 34 is adjusted to a desired amplitude by changing the output of the electric source 42 the variations in the amplitudes of the signals from the other two leads 36 and 38 caused by the variations in each aperture construction can then be eliminated according to the invention. The signals developed from each of the leads 36 and 38 are compared to the standard signal developed from lead 34 and the potentiometers 66 and 68 then, individually are adjusted substantially to eliminate any difference in their amplitudes.

Once the detecting signals from each sensing zone have been balanced the regular operation of the apparatus may proceed with sample suspensions containing unknown particles to be studied. As an example, the solution may be drained through a drain conduit 70 and may be followed by a rinse solution introduced through a rinse conduit 72. Once the bath has been thoroughly rinsed the solution may be drained through the conduit 70 and the next sample may be introduced through the conduit 40. Further details of a sample vessel as shown at 10 may be found in U.S. Pat. No. 3,567,321. The particular type of vessel utilized is not limited within the scope of the invention.

If the particle analyzer 44 includes the circuitry such as described in U.S. Pat. No. 3,549,994, previously mentioned to develop the blood parameters the two adjustments above would be necessary for the RBC and for the WBC parameter determinations. The MCV is determined, however, by using two of the detection signals developed for the RBC so no further adjustments are necessary to develop an accurate MCV parameter.

Thus, instead of the eight previous adjustments, all of which affected the signal to noise ratio of the circuits in the particle analyzer 44 and decreased the sensitivity of the circuits therein, there are now only four adjustments to measure the same three parameters. These adjustments also do not affect the sensitivity or the signal to noise ratio of the circuits in the particle analyzer 44. The device is more sensitive and the information developed by the device is more accurate.

Typically, before the apertures are balanced, the circuits in the particle analyzer 44 will be electronically adjusted for proper operation. Balancing, as taught by the invention, would typically be done with an initial set up and thereafter when desired as long as the aperture combination is not changed. The device would be balanced any time the aperture combination is changed. The invention enables the device to be balanced quickly and accurately whenever a broken aperture tube is replaced or the combination of apertures in parallel is otherwise changed.

Many modifications and variations of the present invention are possible in light of the above teachings. A third potentiometer, identical to potentiometer 66 and 68 could be added to the current path between the electric excitation source 42 and lead 34 if it is desired to individually adjust the current passing through lead 34 also. It is therefore to be understood that within the scope of the appended claims the invention may be practiced otherwise than as specifically described.

What is desired to secure by Letters Patent of the United States is:

1. A method for balancing a particle study device for studying particles in suspension, said device including, means having at least two apertures through which said particles in suspension are passed, means for passing an electric current through said apertures simultaneously with passage of a particle through said apertures, and detecting means responsive to variations of the impedance caused by particle passage for generating electric signals in response to said particle passage, said method including the steps of:
   passing particles in suspension from the same particle suspension through each of said apertures;
   generating signals in response to the passage of said particles; and
   adjusting said current passing through said apertures substantially to equalize said signals.

2. A method as claimed in claim 1 wherein:
   adjusting said current passing through said apertures substantially to equalize said signals, includes adjusting said current passing through all but one of said apertures.

3. In a balancing system for a particle study device for studying particles in suspension, said device including in combination, means having a first number of apertures through which said particles in suspension from the same particle suspension are passed, said first number being at least two, means for passing an electric current through said apertures simultaneously with passage of particles through said apertures, and detecting means responsive to variations of the impedance caused by particle passage for generating electric signals in response to said particle passage, said balancing system comprising:
   adjustment means coupled to said means for passing an electric current for adjusting said current passing through said apertures substantially to equalize said signals.

4. A balancing system as claimed in claim 3 wherein said adjustment means include:
   means for adjusting said current passing through a second number of said apertures, said second number of apertures being one less than said first number of apertures, said means being adjusted so that substantially equal detecting signals are generated upon passage of the same sized particles through each of said first number of apertures.

5. A balancing system as claimed in claim 4 wherein said adjustment means include:
   independent adjustment means coupled between each of said second number of apertures and said means for passing an electric current.

6. A balancing system as claimed in claim 5 wherein said independent adjustment means include:
   variable impedance means.

7. A balancing system as claimed in claim 6 wherein said variable impedance means include:
   potentiometers.

8. A balancing system as claimed in claim 4 wherein said means for passing an electric current include:
   a voltage source.

9. A balancing system as claimed in claim 8 wherein said adjustment means include:
   variable resistance means coupled between each of said second number of apertures and said means for passing an electric current.

10. A balancing system as claimed in claim 9 wherein said variable resistance means include:
    potentiometers.

* * * * *